(12) United States Patent
Hosokawa et al.

(10) Patent No.: US 12,310,658 B2
(45) Date of Patent: May 27, 2025

(54) IMAGE GENERATION APPARATUS, IMAGE GENERATION METHOD, AND PROGRAM

(71) Applicant: NIPPON TELEGRAPH AND TELEPHONE CORPORATION, Tokyo (JP)

(72) Inventors: Kenchi Hosokawa, Tokyo (JP); Kazushi Maruya, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 670 days.

(21) Appl. No.: 17/638,812

(22) PCT Filed: Sep. 2, 2019

(86) PCT No.: PCT/JP2019/034335
§ 371 (c)(1),
(2) Date: Feb. 26, 2022

(87) PCT Pub. No.: WO2021/044454
PCT Pub. Date: Mar. 11, 2021

(65) Prior Publication Data
US 2022/0330812 A1 Oct. 20, 2022

(51) Int. Cl.
*G06T 7/00* (2017.01)
*A61B 3/06* (2006.01)

(52) U.S. Cl.
CPC .......... *A61B 3/063* (2013.01); *G06T 7/0012* (2013.01)

(58) Field of Classification Search
CPC ........ A61B 3/063; A61B 3/022; G06T 7/0012
See application file for complete search history.

(56) References Cited

U.S. PATENT DOCUMENTS

| | | | | |
|---|---|---|---|---|
| 4,293,200 A | * | 10/1981 | Dobson | A61B 3/022 351/239 |
| 4,365,873 A | * | 12/1982 | Ginsburg | A61B 3/06 351/239 |

(Continued)

OTHER PUBLICATIONS

Lesmes et al, "Bayesian Adaptive Estimation of the Contrast Sensitivity Function: The Quick CSF Method," Journal of Vision, vol. 10, No. 3, pp. 1-21, 2010.

(Continued)

*Primary Examiner* — Balram T Parbadia
*Assistant Examiner* — John Curtis Sipes (57) ABSTRACT

A contrast sensitivity measurement apparatus (1) generates a stimulating image to be output to an external display device (20) for measuring contrast sensitivity of a user. An image scale setting unit (12) determines the spatial frequency in units of pixels on the basis of an observation distance, physical characteristics of the external display device (20), and visual characteristics of a human. A carrier waveform generation unit (13) generates a luminance map in which a change of luminance along a first axis follows the spatial frequency. A contrast map generation unit (14) generates a contrast map in which contrast gradually decreases from one end to another end along a second axis, and an equal contrast line forms a given waveform. A stimulating image synthesis unit (15) generates the stimulating image by synthesizing the luminance map and the contrast map.

18 Claims, 7 Drawing Sheets

(56) References Cited

U.S. PATENT DOCUMENTS

| | | | | |
|---|---|---|---|---|
| 6,045,515 | A | * | 4/2000 | Lawton .................. A61B 3/022 351/239 |
| 6,213,956 | B1 | * | 4/2001 | Lawton .................. A61B 3/022 351/239 |
| 2008/0137037 | A1 | * | 6/2008 | Kratzer .................. A61B 3/022 351/243 |
| 2015/0150444 | A1 | * | 6/2015 | Bex .......................... A61B 3/06 351/242 |
| 2017/0273553 | A1 | * | 9/2017 | Greivenkamp, Jr. ........................ A61B 3/0041 |

OTHER PUBLICATIONS

Mulligan, J. B., "A method for rapid measurement of contrast sensitivity on mobile touch-screens," Human Vision and Electronic Imaging 2016, 6 pages.

Hosokawa et al. "Development of visual test kits suitable for daily life and rehabilitation", The 27th Meeting of Japanese Association for Rehabilitation of the Visually Impaired in Kobe, Published Sep. 14, 2018, 2 pages.

Hosokawa et al. "New method for measuring contrast sensitivity curve for tablet PC", Vision Society of Japan, Abstracts of 2019 Winter Meeting, 3p26, Published Jan. 20, 2019, 5 pages.

Hosokawa et al. "New method for measuring contrast sensitivity curve for tablet PC", Vision Society of Japan, 2019, Winter Meeting, Published Jan. 20, 2019, 2 pages.

Hosokawa et al. "Test battery for daily self-assessment of visual abilities", Vision Science Society 2019, Abstract of 19th Annual Meeting, 33.436, Published May 17, 2019, 7 pages.

Hosokawa et al. "Test battery for daily self-assessment of visual abilities", Vision Science Society 2019, 19th Annual Meeting, Published May 17, 2019, 1 page.

Hosokawa et al. "Gamified vision test system for daily self-check", IEEE GEM 2019, Published Jun. 19, 2019, 8 pages.

Hosokawa et al. "Gamification of vision test improves usability for internet experiments", APCV 2019, O2-2-4, Published Jul. 29, 2019, 5 pages.

* cited by examiner

IMAGE GENERATION APPARATUS, IMAGE GENERATION METHOD, AND PROGRAM

CROSS-REFERENCE TO RELATED APPLICATIONS

This application is a U.S. National Stage Application filed under 35 U.S.C. § 371 claiming priority to International Patent Application No. PCT/JP2019/034335, filed on 2 Sep. 2019, the disclosure of which is hereby incorporated herein by reference in its entirety.

TECHNICAL FIELD

The present invention relates to an image generation technology, and in particular, to a technology for generating a stimulating image used for a vision test.

BACKGROUND ART

A vision test is performed in order to find an eye disease for example. A conventional vision test needs a large-scale examination apparatus in a hospital, a laboratory, or the like, and is difficult to perform casually. In order to find an eye disease early, it is desirable to perform self test on a daily basis. Therefore, it is demanded to enable a vision test to be performed easily.

As one type of vision test, measurement of contrast sensitivity is performed. Conventional measurement of contrast sensitivity needs repetition of a large number of tests and takes time. Therefore, reduction of the measurement time is demanded (for example, see Non-Patent Literature 1). For time reduction, a measurement method in which a plurality of images ranging from a high-contrast image to a low-contrast image are presented simultaneously and a visible region in which contrast can be visually recognized is positionally designated has been proposed (for example, see Non-Patent Literature 2).

CITATION LIST

Non-Patent Literature

Non-Patent Literature 1: Lesmes, Luis Andres, et al, "Bayesian Adaptive Estimation of the Contrast Sensitivity Function: The Quick CSF Method," Journal of Vision, vol. 10, no. 3, pp. 1-21, 2010.
Non-Patent Literature 2: Mulligan, J. B., "A method for rapid measurement of contrast sensitivity on mobile touch-screens," Human Vision and Electronic Imaging 2016.

SUMMARY OF THE INVENTION

Technical Problem

However, in the measurement method of Non-Patent Literature 2, since determination of whether or not contrast can be visually recognized depends on the subject of the person being tested, it is impossible to determine whether or not the visible region designated by the person being tested is a reliable answer. Therefore, in order to improve the reliability of contrast sensitivity measurement, it is necessary to perform measurement repeatedly, so that it takes time to obtain a highly reliable measurement result.

In view of the technical problem described above, an object of the present invention is to generate an image from which a contrast sensitivity measurement result having high reliability can be obtained in a short period.

Means for Solving the Problem

An image generation apparatus of a first aspect of the present invention is an image generation apparatus that generates a stimulating image to be output to a display device for measuring contrast sensitivity of a user. The apparatus includes an image scale setting unit that determines a spatial frequency in units of pixels within a range visually recognizable by a human when displayed on the display device, on the basis of an observation distance representing a distance between the display device and the eye of the user, physical characteristics of the display device, and visual characteristics of the human; a carrier waveform generation unit that generates a luminance map in which luminance of each pixel is set in such a manner that a change in the luminance along a first axis of the display device follows the spatial frequency; a contrast map generation unit that generates a contrast map in which contrast of each pixel is set in such a manner that the contrast gradually decreases from one end to another end along a second axis orthogonal to the first axis, and that an equal contrast line linking points having the same contrast forms a given waveform; and a stimulating image synthesis unit that generates the stimulating image by synthesizing the luminance map and the contrast map.

An image generation apparatus of a second aspect of the present invention is an image generation apparatus that generates a stimulating image to be output to a display device for measuring contrast sensitivity of a user. The apparatus includes a carrier waveform generation unit that generates a luminance map in which luminance of each pixel is set in such a manner that a change in the luminance along a first axis of the display device follows a given spatial frequency; a contrast map generation unit that generates a contrast map in which contrast of each pixel is set in such a manner that the contrast gradually decreases from one end to another end along a second axis orthogonal to the first axis, and that an equal contrast line linking points having the same contrast forms a given waveform; and a stimulating image synthesis unit that generates the stimulating image by coloring an image in which the luminance map, the contrast map, and a background image including at least a night sky are synthesized, so as to represent an aurora with respect to a change in the luminance.

Effects of the Invention

According to the present invention, it is possible to generate an image from which a contrast sensitivity measurement result having high reliability can be obtained in a short period.

DESCRIPTION OF EMBODIMENTS

Hereinafter, embodiments of the present invention will be described in detail. Note that in the drawings, components having the same function are denoted by the same reference numeral, and overlapping description is omitted.

[Contrast Sensitivity Measurement Test]

Figure 1:
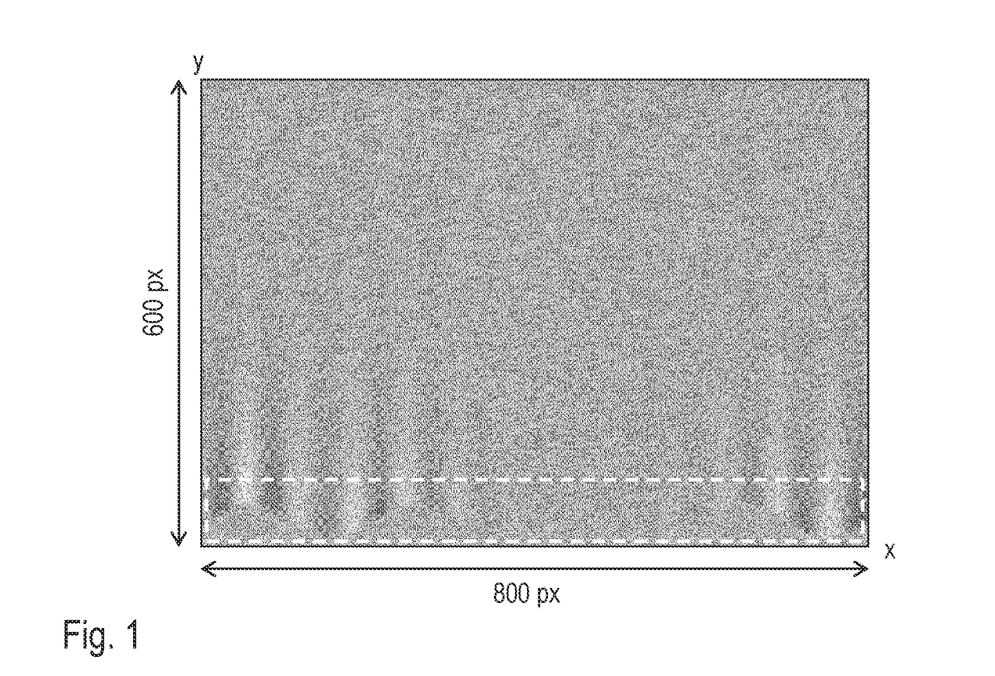
FIG. 1 shows an example of a stimulating image.
Figure 2:
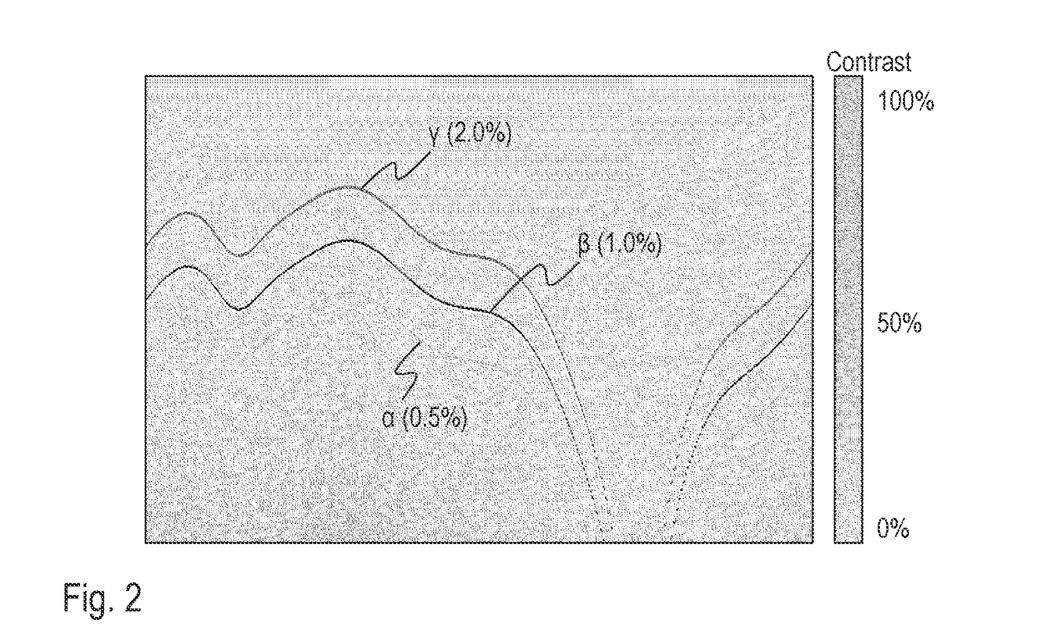
FIG. 2 shows an example of a contrast map.

First, a contrast sensitivity measurement test of the present invention will be described conceptually. In the contrast sensitivity measurement test of the present invention, one image in which contrast is gradually changed from a high-contrast part to a low-contrast part (hereinafter referred to as a "stimulating image") is presented to a user, and the user designates a range in which the contrast can be visually recognized on the stimulating image, whereby the contrast sensitivity of the user is measured. FIG. 1 is an example of a stimulating image generated in the present invention. The stimulating image of FIG. 1 is formed of a rectangle having 800×600 pixels. In the stimulating image of FIG. 1, the luminance changes with a single spatial frequency in the horizontal axis (hereinafter also referred to as "x axis") direction, and the contrast gradually decreases with a logarithmic scale from the lower end to the upper end in the vertical axis (hereafter also referred to as "y axis") direction. At that time, a change in the contrast of a pixel array at the lower end of the image is set according to a given waveform. Thereby, as illustrated in FIG. 2, a line linking points having the equal contrast on the stimulating image (hereinafter also referred to as an "equal contrast line") is set so as to form a waveform. According to FIG. 2, it is found that a line α linking points where contrast is 0.5%, a line β linking points where contrast is 1.0%, and a line γ linking points where contrast is 2.0% are arranged vertically while forming similar waveforms.

A user is instructed to trace a boundary line of a visible region in which contrast can be visually recognized on the stimulating image. For implementation, it is expected that the user traces the boundary line by operating a mouse or a touch panel on the stimulating image displayed on a computer screen. Since the boundary line represents a limit value of the contrast that can be visually recognized by the user, it is possible to estimate the contrast sensitivity of the user by statistically processing the contrast of respective points on the boundary line. In the conventional technology, only one measurement result is obtained from one test. However, in this method, since one point on the boundary line corresponds to one test, a plurality of measurement results can be obtained from one test using one stimulating image.

For example, it is expected that the reliability of the measurement result may be low such as the case where the motivation of the user is low so that the user traces half-heartedly, or the case where the apparatus operation skill is low. Therefore, even in the case of using the present method, it is desirable to perform the test a plurality of times in order to improve the reliability of the measurement result. However, since a plurality of measurement results can be obtained from one test, the number of required tests can be reduced compared with the conventional case.

Moreover, from the viewpoint of improving reliability of the measurement result, in the present invention, it is possible to introduce a system for increasing the motivation of the user, correcting the measurement result on the basis of the apparatus operation skill, or the like.

CONFIGURATIONS OF EMBODIMENTS

Hereinafter, two embodiments will be described. A first embodiment is a stimulating image generation method for generating a stimulating image to be used for measuring contrast sensitivity by a contrast sensitivity measurement apparatus. A second embodiment is a contrast sensitivity measurement method of calculating a measurement result of contrast sensitivity from response data of a user acquired using a stimulating image generated by the stimulating image generation method of the first embodiment by a contrast sensitivity measurement apparatus.

[Contrast Sensitivity Measurement Apparatus]

Figure 3:
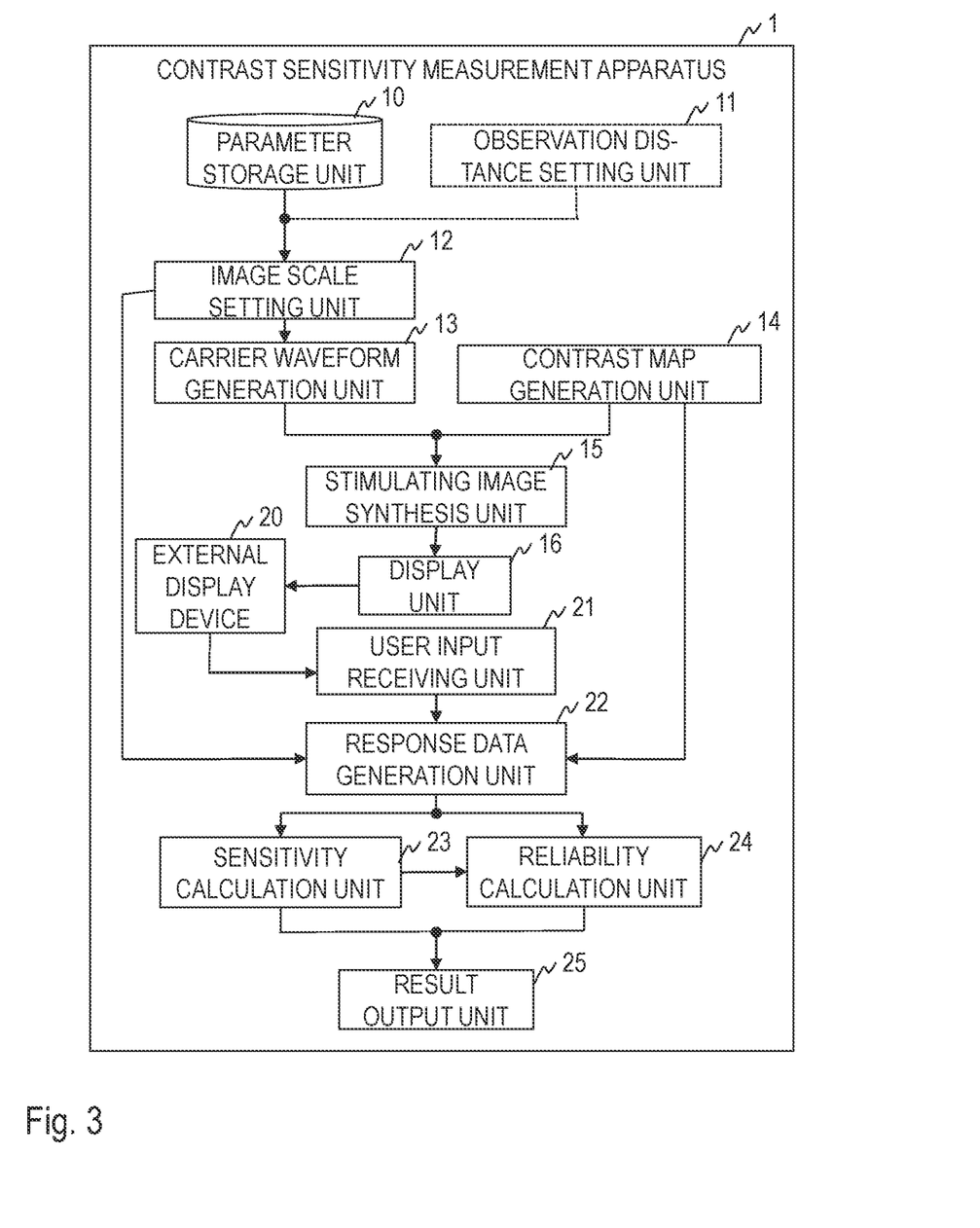
FIG. 3 is a diagram illustrating a functional configuration of a contrast sensitivity measurement apparatus.

A contrast sensitivity measurement apparatus of the embodiment is an information processing apparatus that generates a stimulating image for measuring contrast sensitivity and presents it to a user, and calculates contrast sensitivity on the basis of an input from the user. As illustrated in FIG. 3, a contrast sensitivity measurement apparatus 1 includes a parameter storage unit 10, an image scale setting unit 12, a carrier waveform generation unit 13, a contrast map generation unit 14, a stimulating image synthesis unit 15, a display unit 16, an external display device 20, a user input receiving unit 21, a response data generation unit 22, a sensitivity calculation unit 23, a reliability calculation unit 24, and a result output unit 25. The contrast sensitivity measurement apparatus 1 may further include an observation distance setting unit 11, as illustrated in FIG. 3. The contrast sensitivity measurement apparatus 1 executes the processing of the respective steps illustrated in FIG. 4, whereby the stimulating image generation method of the first embodiment is implemented. Further, the contrast sensitivity measurement apparatus 1 executes the processing of the respective steps illustrated in FIG. 5, whereby the contrast sensitivity measurement method of the second embodiment is implemented.

The contrast sensitivity measurement apparatus 1 is a special apparatus configured such that a special program is read in a publicly-known or dedicated computer having a central processing unit (CPU), a main memory (random access memory (RAM)), and the like. The contrast sensitivity measurement apparatus 1 executes the processing under control of the CPU. Data input to the contrast sensitivity measurement apparatus 1 and data obtained in the processing are stored in the main memory for example, and the data stored in the main memory is read out to the central processing unit as required and is used for other processing. At least part of the contrast sensitivity measurement apparatus 1 may be configured of hardware such as an integrated circuit. The storage units provided to the contrast sensitivity measurement apparatus 1 may be configured of a main memory such as a random access memory (RAM), an auxiliary storage device configured of a hard disk, an optical disk, or a semiconductor memory element such as a flash memory, or middleware such as a relational database or a key value store. Specifically, the contrast sensitivity measurement apparatus 1 is an information processing apparatus having an input function such as a mouse or a touch panel and an output function such as a display or a printer, such as a mobile terminal like a smartphone or a tablet, or a desktop or laptop personal computer.

First Embodiment: Generation of Stimulating Image for Contrast Sensitivity Measurement Hereinafter, a processing procedure of a stimulating image generation method of the first embodiment, to be executed by the contrast sensitivity measurement apparatus 1, will be described with reference to FIG. 4.

Figure 4:
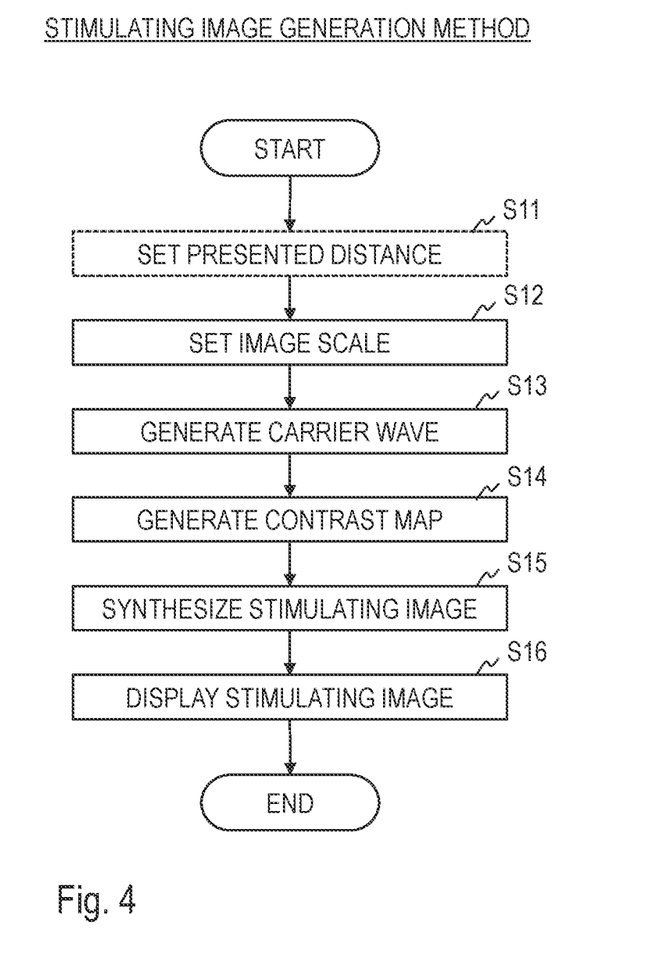
FIG. 4 is a diagram illustrating a processing procedure of a stimulating image generation method.

In the parameter storage unit 10, predetermined parameters used for generating a stimulating image are stored. Specifically, as the predetermined parameters, a spatial frequency parameter, a spatial frequency measurement range, and device characteristics are stored in advance. The predetermined parameters may include an observation distance.

The spatial frequency parameter is at least one spatial frequency representing stripe stimulus displayed on the stimulating image. The spatial frequency means, in the case where a position and a distance on the field of view to be viewed are represented by the viewing angle by means of trigonometry, an inverse number of the waveform of the viewing angle display. The unit is cycle/deg (the number of cycles entering in 1 degree of viewing angle). The spatial frequency may take a fixed value, or may be an output of a function to which FM modulation is applied along the x axis. The spatial frequency included in the spatial frequency parameter is selected at random from a plurality of fixed value arrays or function outputs prepared in advance. In the case of generating a stimulating image with a single spatial frequency, the spatial frequency parameter is configured of one spatial frequency, while in the case of generating a stimulating image so as to include a plurality of spatial frequencies, the spatial frequency parameter is configured of an array of a plurality of spatial frequencies.

The spatial frequency measurement range is a range of spatial frequencies having the meaning for measuring contrast sensitivity in view of human visual characteristics. Specifically, it is a range of spatial frequencies measured in the contrast sensitivity measurement experiment described in Reference Literature 1 provided below, for example. Typically, the range of the spatial frequency is between 0.02 cycle/deg and 30 cycle/deg. In the case of performing measurement for the purpose of comparing visual characteristics of persons, a range from 0.04 cycle/deg to 15 cycle/deg is sufficient.

[Reference Literature 1] Campbell, F. W., & Robson, J. G., "Application of Fourier analysis to the visibility of gratings," The Journal of physiology, Vol. 197(3), pp. 551-566, 1968.

The device characteristics are physical characteristics of the external display device 20 that displays a stimulating image. For example, when the external display device 20 is a typical display device (for example, liquid crystal display) of an electronic apparatus, the device characteristics indicate the size of the entire display device and the size of one pixel in the display device.

The observation distance indicates the distance between the eye of a user and a stimulating image when the user observes the stimulating image. As the observation distance, a predetermined fixed value may be given, or an observation distance setting unit 11 may be provided so as to automatically compute it from another parameter. The observation distance is presented to the user, and the user is instructed to observe the stimulating image from a position separated by the distance. At that time, a proximity sensor or a range finder (not shown) may be used to measure the distance between the eye of the user and the external display device 20, and the user may be instructed to move the face close or away to make the distance close to the observation distance.

The observation distance setting unit 11 computes the observation distance as described below. First, the observation distance setting unit 11 calculates a wavelength range that can be presented by the device, from the device characteristics. The lower limit of the wavelength range is given from the size of one pixel, and the upper limit thereof is given from the entire size. Then, the observation distance setting unit 11 calculates, by the trigonometry, an observation distance in which the spatial frequency corresponding to the wavelength range becomes equal to the spatial frequency parameter when viewed from the user and which falls within the spatial frequency measurement range.

The external display device 20 must have physical characteristics sufficient for displaying a stimulating image in the spatial frequency measurement range. For example, in a typical display of a personal computer in which the width of the screen is 50 cm and the resolution is 1920×1080 pixels, when the observation distance is 48 cm, the maximum spatial frequency that can be displayed is 16 cycle/deg with the wavelength of 2 pixels.

At step S12, the image scale setting unit 12 reads the spatial frequency parameter, the device characteristics, the spatial frequency measurement range, and the observation distance from the parameter storage unit 10, and determines a set of a wavelength w and a spatial frequency f in units of pixels within a range in which a human can visually recognize when displayed on the external display device 20. The image scale setting unit 12 outputs the determined set of the wavelength w and the spatial frequency f to the carrier waveform generation unit 13.

At step S13, the carrier waveform generation unit 13 receives the set of the wavelength w and the spatial frequency f from the image scale setting unit 12, and generates a luminance map that is a two-dimensional image in which luminance of each pixel is set such that the luminance is changed in a sine-wave shape or an FM-modulated sine-wave shape in the x axis direction. At that time, the wavelength of the sine wave becomes the input wavelength w, and the phase may be turned into a random number. As the random number, a numerical value of a real number may be determined on the basis of a pseudorandom number computed by a computer or a physical random number array input to a computer. A random number to be used in other processing may be generated similarly, which will not be particularly described below. In the case of generating a stimulating image so as to include a plurality of spatial frequencies, the luminance map is generated such that the wave number of each spatial frequency is 2 or larger. Here, an example in which the luminance is changed in the x axis direction is shown. However, the present invention is not limited thereto. It is also possible to generate a luminance map in which the luminance is changed in any axis direction. Hereinafter, an axis along which the luminance is changed is also referred to as a "first axis". The carrier waveform generation unit 13 outputs the generated luminance map to the stimulating image synthesis unit 15.

Specifically, the carrier waveform generation unit 13 generates the luminance map as described below. For example, in the case of generating the luminance map with a single spatial frequency, luminance L(x, y) at coordinates x, y for all pixels is calculated from the following expression, where w represents a wavelength in units of pixels, r represents a random number indicating the phase, and the luminance range is 0 or larger and 1 or smaller.

$$L(x, y) = 0.5 + 0.5 * \sin\left(2\pi\left(\frac{x}{w}\right) + r\right) \quad \text{[Math. 1]}$$

At step S14, the contrast map generation unit 14 generates a contrast map that is a two-dimensional image in which contrast of each pixel is set. In the contrast map, the contrast of each pixel is set such that the contrast gradually decreases from the lower end to the upper end in the y axis direction and an equal contrast line forms a predetermined waveform. Here, an example in which contrast gradually decreases from the lower end to the upper end in the y axis direction is shown. However, the present invention is not limited thereto. It is only necessary that contrast gradually decreases from one end to the other end along an axis orthogonal to the first axis. That is, when the first axis is the y axis for example, the contrast may gradually decrease from the lower end to the upper end (or from the upper end to the lower end) in the x axis direction. Meanwhile, when the first axis is the x axis, the contrast may gradually decrease from the upper end to the lower end (or from the lower end to the upper end) in the y axis direction. Hereinafter, the axis along which the contrast gradually decreases is also referred to as a "second axis". The contrast map generation unit 14 outputs the generated contrast map to the stimulating image synthesis unit 15.

Specifically, the contrast map generation unit 14 generates a contrast map by calculating contrast of each pixel from a contrast calculation formula satisfying the following definitions (1) to (3).

(1) It is assumed that contrast of one pixel decreases at a certain rate with respect to contrast of another pixel adjacent thereto in a downward y-axis direction. At that time, it is assumed that the contrast at the lower end of the contrast map is higher than 0.1, and the contrast at the upper end of the contrast map is 0.002 or lower. For example, it is preferable that the contrast at the lower end of the contrast map is 0.25 or higher and the contrast at the upper end of the contrast map is 0.001 or lower.

(2) Contrast at the lower end of the contrast map is defined by a complex wave. A complex wave includes at least a component in which the wavelength is almost equal to the image width and the amplitude is 0.5 or more (hereinafter also referred to as a "dip component") and a component in which the wavelength is ½ to ⅛ of the image width and the amplitude is about 0.2 (hereinafter also referred to as a "small amplitude component").

(3) The phase and the wavelength of a waveform defining the contrast at the lower end of the contrast map are changed by a random number. In order to prevent the peak of the sine wave of the dip component from being located at both ends of the contrast map in the x axis direction or in the vicinity of the both ends, it is set that a reminder when the phase is divided by 360 degrees becomes 0 to 180 degrees.

An example of the contrast calculation formula satisfying the definitions (1) to (3) will be shown below. For example, when a complex wave is defined by two sine waves, contrast $C(x, y)$ at coordinates x, y for all pixels are calculated from the following expression, where a represents a variable per pixel in the y axis direction, $w_2$ represents the wavelength of a dip component, $r_2$ represents a random number serving as the phase of the dip component, $w_1$ represents the wavelength of a small amplitude component, $r_1$ represents a random number serving as the phase of the small amplitude component, and the range of the contrast is from 0 or larger to 1 or smaller.

$$C(x, y) = \quad \text{[Math. 2]}$$

-continued
$$a^y * 0.5 + 0.5\left(0.2 * \sin\left(2\pi\left(\frac{x}{w_1}\right) + r_1\right)\right) + \sin\left(2\pi\left(\frac{x}{w_2}\right) + r_2\right)$$

While the method of generating a contrast map in a quadrangular shape has been described in this example, the map may be generated in a circular shape. In that case, in a contrast map generation formula, coordinates x, y of an orthogonal coordinate system may be replaced with a drift angle 9 and a radius vector r of a polar coordinate system.

At step S15, the stimulating image synthesis unit 15 receives the luminance map from the carrier waveform generation unit 13 and receives the contrast map from the contrast map generation unit 14, and synthesizes the luminance map and the contrast map to thereby generate a stimulating image. Specifically, presented stimulus $I(x, y)$ is calculated for all pixels by the following expression, where $L(x, y)$ represents a luminance map of coordinates x, y and $C(x, y)$ represents a contrast map of coordinates x, y.

$$I(x,y)=b*(0.5+C(x,y)*(L(x,y)-0.5)) \quad \text{[Math. 3]}$$

Here, b represents a positive constant less than 1, and is set such that the maximum value of the presented stimulus $I(x, y)$ becomes the maximum contrast that can be displayed on the external display device 20. Since each of $L(x, y)$ and $C(x, y)$ takes a value that is 0 or larger and 1 or smaller, the part of the expression except for b takes a value that is 0 or larger and 1 or smaller. This is because an image having the contrast of 1 cannot be displayed on a typical display. The stimulating image synthesis unit 15 outputs the generated stimulating image to the display unit 16.

At step S16, the display unit 16 receives the stimulating image from the stimulating image synthesis unit 15, and performs control to display the stimulating image on the external display device 20. At that time, it is necessary to calibrate the external display device 20 or perform calibration in the processing of the display unit 16 such that the electronical luminance value shown by the presented stimulus and the luminance on the external display device 20 are in linear proportion to each other.

Modification 1 of First Embodiment: Addition of Tracing Accuracy Measurement Element In the contrast sensitivity measurement test that is the subject of the present invention, it is expected to operate a mouse or a touch panel on a computer screen to select a contrast visible region. Therefore, the skill of operating the apparatus by a user may affect the accuracy of the measurement result. Accordingly, it is considered to measure how accurately a user can select an intended part (hereinafter also referred to as "tracing accuracy") simultaneously each time of testing, and to use it for evaluation of the measurement result.

In that case, the contrast map generation unit 14 generates a contrast map so as to include a drastic contrast change that is recognized as a boundary line by many people (hereinafter also referred to as "tracing accuracy measurement element"). For example, in the stimulating image illustrated in FIG. 1, a portion where vertical stripe patterns are clearly visible (a portion surrounded by a broken line) exists in the vicinity of the lower end of the image. When a tracing accuracy measurement element is included in a stimulating image, specifically, the contrast map generation unit 14 sets a contrast map such that a range where contrast decreases drastically is provided in a portion where tracing for contrast measurement is not performed, and that a line linking the starting points of the reduction (that is, "tracing accuracy measurement element") forms a curved line. Here, "decrease drastically" means that the contrast of a pixel decreases in a rate of, for example, about one hundred times "a certain rate" defined in Definition (1), with respect to the contrast of a pixel adjacent on the y axis. The tracing accuracy measurement element includes a component in the same range as a small amplitude component in the complex wave of Definition (2).

Modification 2 of First Embodiment: Generation of Aurora Image

The stimulating image synthesis unit 15 may generate an image in which a background image including at least a night sky, in addition to the luminance map and the contrast map, are synthesized, and generate a stimulating image by coloring the synthesis image to represent an aurora with respect to the change in the luminance. The stimulating image generated in this way becomes an image as if the aurora appears in the night sky. When such an image is presented, a user can take a contrast sensitivity measurement test with a feeling of playing a game. Therefore, it is expected to enhance the motivation of a user to take the contrast sensitivity measurement test, and to achieve an effect of improving the reliability of the test result.

Second Embodiment: Measurement of Contrast Sensitivity

Figure 5:
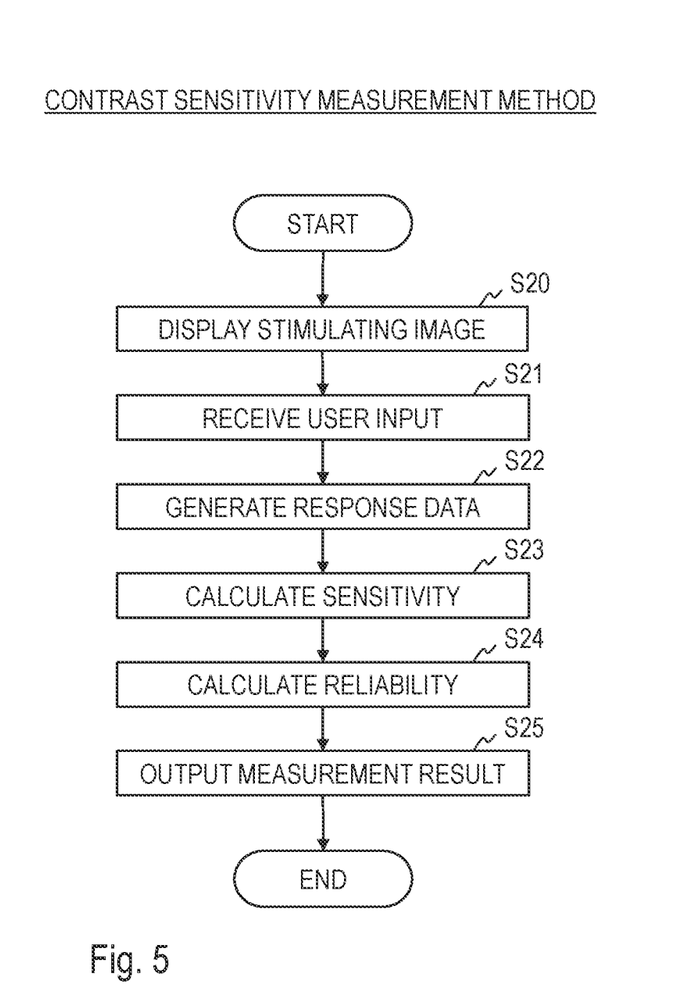
FIG. 5 is a diagram illustrating a processing procedure of a contrast sensitivity measurement method.

Hereinafter, a processing procedure of a contrast sensitivity measurement method of a second embodiment, to be executed by the contrast sensitivity measurement apparatus 1, will be described with reference to FIG. 5.

At step S20, the external display device 20 displays a stimulating image generated by the stimulating image synthesis unit 15 under control of the display unit 16. A user observes the presented stimulating image, and traces the boundary line of a visible region where contrast is visually recognized, with use of a mouse or a touch panel, in accordance with an instruction by the contrast sensitivity measurement apparatus 1.

At step S21, the user input receiving unit 21 receives as an input of a tracing operation by the user on the stimulating image, and generates a coordinate array (hereinafter also referred to as "input data") representing the boundary line of the visible region where contrast can be visually recognized. The input data is an array $[x_1, y_1, x_2, y_2, \ldots, x_n, y_n]$ of n pieces of coordinates selected such that x coordinates are set at equal intervals among the points through which the line traced by the user passes on the stimulating image. Here, n represents the number of coordinates identifying the tracing operation. The user input receiving unit 21 outputs the generated input data to the response data generation unit 22.

Specifically, the user input receiving unit 21 first divides x coordinates by a certain width, and sets n pieces of windows. The width of a window is the number of pixels of an average finger width on the touch panel, for example. Input coordinates that are touched or clicked are monitored regularly, and the value of a y coordinate corresponding to each window is paired with the value of an x coordinate corresponding to the window and recorded. When the pixel selected on the touch panel or the like has a width, a value at the center of the selected region may be recorded. Moreover, when a plurality of touches or clicks are input with respect to a window, the recorded coordinates are updated. For a window with no touch or click, not-a-number (NaN) is designated so as to be distinguishable. When coordinates corresponding to a predetermined number of windows are recorded or when an input completion signal is input by a user through the input completion operation or the like, the coordinates having been recorded so far are output as an array.

In the case where the contrast map generation unit 14 generates a contrast map in a circular shape, it is only necessary to take a window with an angle ϕ from the center in the polar coordinate display instead of dividing the windows by the x coordinate, and record the distance r from the center.

At step S22, the response data generation unit 22 receives a spatial frequency parameter from the image scale generation unit 12, a contrast map from the contrast map generation unit 14, and input data $[x_1, y_1, x_2, y_2, \ldots, x_n, y_n]$ from the user input receiving unit 21. Then, the response data generation unit 22 generates contrast sensitivity information $[s_1, s_2, \ldots, s_n]$ and spatial frequency information $[f_1, f_2, \ldots, f_n]$ (hereinafter also referred to as "response data") corresponding to the respective coordinates included in the input data. Here, coordinates $x_i, y_i$ (i=1, 2, . . . , n), the contrast sensitivity information $s_i$, and the spatial frequency information $f_i$ correspond to one another when the suffix i is the same. Specifically, for the respective coordinates $x_i, y_i$ included in the input data, the response data generation unit 22 refers to the contrast map, and acquires the contrast presented on the coordinates $x_i, y_i$ as the contrast sensitivity information $s_i$. Then, the response data generation unit 22 refers to the spatial frequency parameter, and acquires the spatial frequency presented on the window including the coordinate $x_i$ as the spatial frequency information $f_i$. The response data generation unit 22 outputs the generated response data to the sensitivity calculation unit 23 and the reliability calculation unit 24.

At step S23, the sensitivity calculation unit 23 receives the response data from the response data generation unit 22, and calculates mean contrast sensitivity $[\mu_1, \mu_2, \ldots, \mu_f]$ for each frequency band. The sensitivity calculation unit 23 outputs the calculated mean contrast sensitivity $[\mu_1, \mu_2, \ldots, \mu_f]$ to the reliability calculation unit 24 and the result output unit 25.

Specifically, the sensitivity calculation unit 23 calculates the mean contrast sensitivity as described below. First, the sensitivity calculation unit 23 divides the wavelength band according to the bandwidth of the spatial frequency channel in the human visual processing, and divides the contrast sensitivity information included in the response data into groups. For example, since the bandwidth of the human spatial frequency channel is about ±1 octave, the contrast sensitivity information may be divided into groups by 0.5 octave in consideration of a safety factor. Then, the sensitivity calculation unit 23 calculates, for each group, a geometric mean in the group of the contrast sensitivity. A geometric mean $\mu_f$ in the group of the frequency f is calculated from the following expression, where $s_i$ represents the contrast sensitivity information, and $k_f$ represents the number of pieces of contrast sensitivity information in the group after being grouped by each spatial frequency.

[Math. 4]
$$\log(\mu_f) = \frac{1}{k_f} \sum_{i=1}^{k_f} \log(s_i)$$

At step S24, the reliability calculation unit 24 receives the response data from the response data generation unit 22 and receives the mean contrast sensitivity from the sensitivity calculation unit 23, and calculates geometric standard deviation for each frequency band to generate reliability [$SD_1$, $SD_2$, ..., $SD_f$]. The reliability calculation unit 24 outputs the calculated reliability [$SD_1$, $SD_2$, ..., $SD_f$] to the result output unit 25.

Specifically, the reliability calculation unit 24 calculates the reliability as described below. First, similar to the sensitivity calculation unit 23, the reliability calculation unit 24 divides the contrast sensitivity information into groups, and for each group, calculates geometric standard deviation in the group of the contrast sensitivity. The reliability calculation unit 24 calculates geometric standard deviation $SD_f$ in the group of the frequency f from the following expression, where $s_i$ represents the contrast sensitivity information, n represents the number of elements in the group, and $\mu_f$ represents the geometric mean in the group of the frequency f.

$$SD_f = \sqrt{\frac{1}{k_f}\sum_{i=1}^{k_f}(\log(s_i) - \log(\mu_f))^2} \qquad \text{[Math. 5]}$$

At step S24, the result output unit 25 receives the mean contrast sensitivity [$\mu_1$, $\mu_2$, ..., $\mu_f$] from the sensitivity calculation unit 23, and receives the reliability [$SD_1$, $SD_2$, ..., $SD_f$] from the reliability calculation unit 24. Then, the result output unit 25 puts the mean contrast sensitivity [$\mu_1$, $\mu_2$, ..., $\mu_f$] and the reliability [$SD_1$, $SD_2$, $SD_f$] into a set, and outputs the set as a measurement result of the contrast sensitivity.

Modification 1 of Second Embodiment: Correction by Tracing Accuracy

The reliability calculation unit 24 has performed processing based on the premise that an output by the user input receiving unit 22 is correct. However, variation may be caused by the grounds other than user determination, depending on the accuracy of user input. The grounds for causing variation may include the width of a finger of a user who makes an input on the touch panel, pointing accuracy of the mouse or the touch panel, and the like. In order to correct such variation, a tracing accuracy measurement element is included in the stimulating image, whereby the tracing accuracy of a user is measured.

Specifically, first, a user is also required to trace the tracing accuracy measurement element, so that the user input receiving unit 21 obtains tracing coordinate information that is less likely to depend on the user's criterion for determination. Then, the result output unit 25 obtains standard deviation of the difference between the coordinates of the tracing accuracy measurement element and the tracing coordinate information, as tracing accuracy. Finally, the result output unit 25 normalizes the output of the reliability calculation unit 24 with the tracing accuracy. Thereby, it is possible to eliminate variation caused by the grounds other than the determination by the user from the reliability, and to obtain more accurate reliability.

Modification 2 of Second Embodiment: Calculation of Adoption/Non-Adoption Level

It may be configured that if the reliability output by the reliability calculation unit 24 is low reliability that seldom appears, the corresponding contrast sensitivity may not be adopted. "Low reliability that seldom appears" may be determined corresponding to the accuracy according to the purpose of measurement. For example, it is set that reliability separated from the average of the previously collected reliability by two times or more the standard deviation is used as a threshold.

Specifically, for each reliability, the result output unit 25 calculates an adoption/non-adoption level indicating whether or not to adopt the corresponding contrast sensitivity. The result output unit 25 outputs only contrast sensitivity information to be adopted on the basis of the adoption/non-adoption level. Alternatively, the result output unit 25 may output a measurement result of the contrast sensitivity while adding thereto the adoption/non-adoption level corresponding to each reliability.

Modification 3 of Second Embodiment: Correction by Regression Formula

It is considered that the reliability reflects the operation skill and the motivation of the user, and also reflects the tendency of determining to be "visible" by the user. By correcting the contrast sensitivity on the basis of the tendency of determining to be "visible" by the user, it is possible to obtain a value close to the contrast sensitivity measured by a stricter method. More specifically, a co-vary relationship between the parameter and the reliability that is estimated when the contrast sensitivity obtained with a plurality of spatial frequencies is put into a specific equation is obtained, and contrast sensitivity of the case where reliability is assumed to be high according to the regression formula of the parameter and the reliability having a high co-vary relationship is estimated.

A specific equation is, for example, the following expression approximating the relationship between the spatial frequency f and the contrast sensitivity S(f).

$$S'(f) = \log_{10}(\gamma_{max}) + K\left(\frac{\log_{10}(f) - \log_{10}(f_{max})}{\frac{\beta'}{2}}\right)^2 \qquad \text{[Math. 6]}$$

$$S(f) = S'(f),$$

$$f \geq f_{max}$$

$$S(f) = \log_{10}(\gamma_{max}) - \delta,$$

$$f < f_{max}$$

and $$S'(f) < \gamma_{max} - \delta$$

Here, $f_{max}$ represents a spatial frequency having the best contrast sensitivity, $\gamma_{max}$ represents the best contrast sensitivity, $\beta'$ represents a half value width in a parabola shown by the term including it, and $\delta$ represents a lower limit value of the contrast sensitivity in a region of low spatial frequency. The parameters are, for example, $f_{max}$, $\gamma_{max}$, $\beta'$, and $\delta$ when put into the equations described above. Note that the specific equations described above are examples. While the specific equations are described as two-dimensional functions, the functions are not limited thereto.

The co-vary relationship between the parameter and the reliability can be obtained by collecting a plurality of pieces of contrast sensitivity in advance, and obtaining from an arbitrary parameter and reliability in the case of putting into the specific equation. The regression formula between the parameter and the reliability is obtained by, for example, applying linear regression to any one parameter when a measurement result is put into a specific equation and the reliability of the measurement result. Note that the regression described above is an example. Moreover, while linear regression is described above, a regression function is not limited thereto.

The result output unit 25 performs correction by the regression formula on the reliability as described below. First, the result output unit 25 obtains a difference between an estimation value of a parameter obtained by substituting the reliability in a measurement into the regression formula and an actual parameter in the measurement. Then, the result output unit 25 substitutes the value, obtained by adding the difference to the estimation value of the parameter when the reliability is sufficiently high, as a parameter into a specific equation, and obtains a value of the contrast sensitivity after the correction.

Modification 4 of Second Embodiment:
Combination

Since each of Modifications 1 to 3 of the second embodiment is independent processing, any one of them may be implemented or a plurality of them may be implemented simultaneously. However, in the case of implementing a plurality of modifications by combining them, it is required to take caution with the application sequence. Specifically, application should be made in the order of Modifications 1 to 3 in preference. For example, in the case of applying all of Modifications 1 to 3, first, correction by the tracing accuracy is made, and adoption/non-adoption is determined with respect to the reliability after the correction, and correction by the regression formula should be made only to the corrected reliability to be adopted. By applying Modification 1 in preference, it is possible to correct the low accuracy in the answer caused by low tracing accuracy, and to evaluate the reliability of determination from the visual stimulation with higher accuracy. Correction in Modification 3 is not always applicable if the reliability is very low. Therefore, in order not to apply correction to such a measurement result, it is necessary to previously perform calculation of the adoption/non-adoption level of Modification 2.

[Experimental Result]

Figure 6:
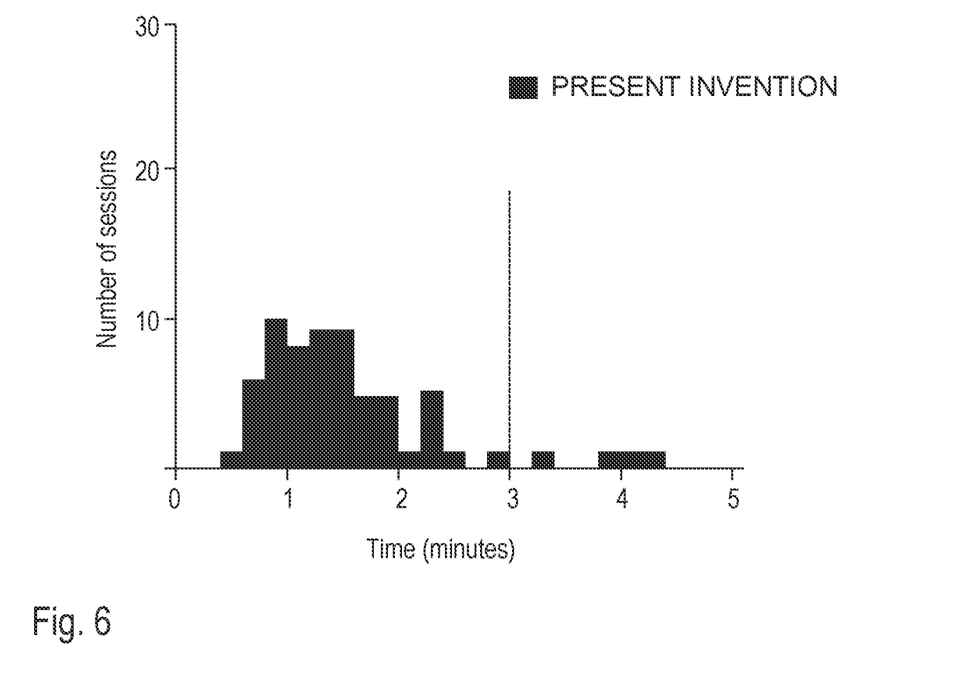
FIG. 6 is a diagram for explaining an experimental result.
Figure 7:
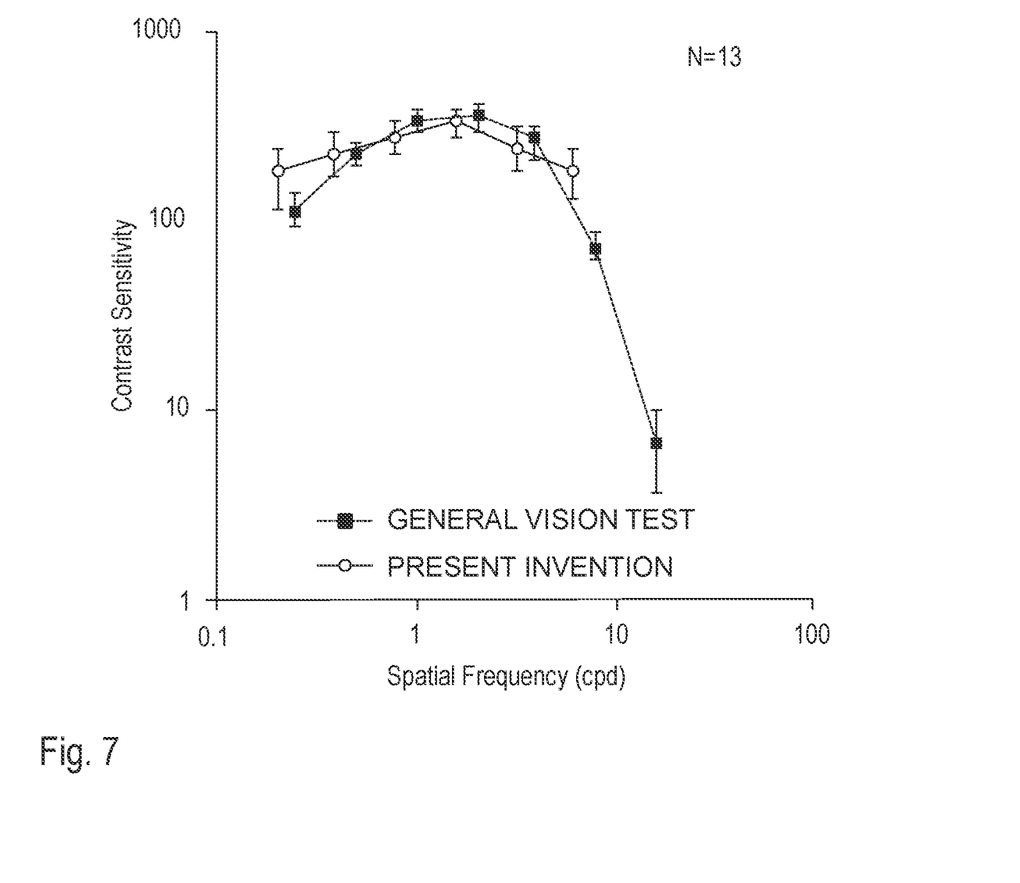
FIG. 7 is a diagram for explaining an experimental result.

FIGS. 6 and 7 illustrate experiment results showing the effect of the present invention.

FIG. 6 is a graph in which the periods of time required for the contrast sensitivity measurement test of the present invention are compared. It is found that the test is completed in a little longer than one minute in most cases in the present invention. Meanwhile, in Non-Patent Literature 1, it is asserted that the time required for contrast sensitivity measurement that was taken for 30 to 60 minutes conventionally could be reduced to 10 to 20 minutes. That is, according to the present invention, a measurement result of contrast sensitivity can be obtained in a shorter time than any of the conventional technologies.

FIG. 7 is a graph in which accuracy of the contrast sensitivity obtained in the present invention and that obtained in a general vision test are compared. In FIG. 7, in the present invention and a general vision test, the same person being tested took a plurality of tests while changing the spatial frequency, and the contrast sensitivity obtained at each spatial frequency is plotted. From FIG. 7, it is found that in the measurement result of the present invention, a contrast measurement result equivalent to that of the general vision test is obtained. That is, according to the present invention, a measurement result of contrast sensitivity equivalent to that of a general vision test can be obtained in a shorter time.

While embodiments of the present invention have been described above, the specific configuration is not limited to that in the embodiments. It is needless to say that any appropriate changes in design within a scope not deviating from the spirit of the present invention are included in the present invention. The respective types of processing described in the embodiments may be performed not only in a time-series manner according to the sequence described above but may be performed in parallel or individually according to the processing capacity of the device that performs the processing or as required.

[Program, Recording Medium]

Figure 8:
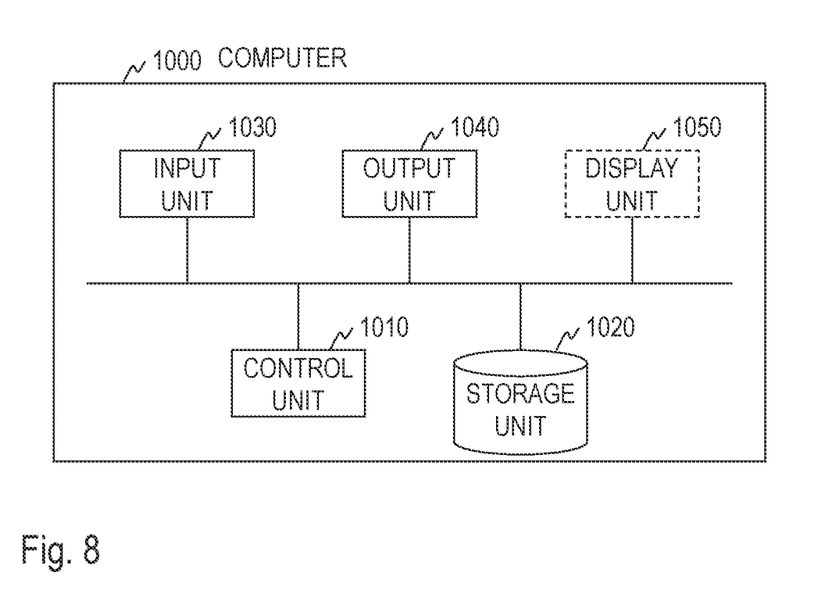
FIG. 8 is a diagram illustrating a functional configuration of a computer.

In the case of implementing the respective types of processing functions in the respective devices described in the embodiments by a computer, the processing contents of the functions that should be held by the respective devices are described by a program. Then, when a storage unit 1020 of the computer illustrated in FIG. 8 is allowed to read the program, and a control unit 1010, an input unit 1030, an output unit 1040, and the like are allowed to operate, the processing functions of the respective types in the respective devices are implemented on the computer.

The program describing the processing contents can be recorded on a computer-readable recording medium. A computer-readable recording medium may be, for example, a magnetic recording device, an optical disk, a magneto-optical recording medium, a semiconductor memory, or the like.

Moreover, distribution of the program is performed by selling, assigning, lending, or the like a portable recording medium such as a DVD or a CD-ROM on which the program is recorded. Furthermore, it is acceptable to have a configuration in which the program may be distributed by being stored on a storage device of a server computer and transferring the program from the server computer to another computer over a network.

A computer that executes such a program first stores the program recorded on a portable recording medium or the program transferred from a server computer, in the storage device of the own, for example. Then, at the time of executing the processing, the computer reads the program stored in the storage device of the own, and executes processing according to the readout program. Further, as another execution mode of the program, the computer may read the program directly from a portable recording medium and execute the processing according to the program, or each time the program is transferred to the computer from a server computer, the computer may sequentially execute the processing according to the received program. Furthermore, it is also possible to have a configuration of executing processing described above by a service in which a processing function is implemented only by the execution instruction and acquisition of the result, that is, a so-called application service provider (ASP) type service, without transferring the program to the computer from the server computer. Note that the program of the present mode includes information to be provided for processing by a computer and is equivalent to the program (such as data that is not a direct instruction to the computer but has a nature of defining processing by the computer).

Further, while it is described that the present apparatus is configured by execution of a predetermined program on the computer in this mode, at least part of the processing content may be implemented by hardware.

The invention claimed is:

1. An image generation apparatus that generates a stimulating image to be output to a display device for measuring contrast sensitivity of a user, the apparatus comprising a processor configured to execute operations comprising:
   determining a spatial frequency in units of pixels within a range visually recognizable by a human when displayed on the display device, on a basis of an observation distance representing a distance between the display device and an eye of the user, a physical characteristic of the display device, and a visual characteristic of the human;
   generating a luminance map in which luminance of each pixel is set in such a manner that a change in the luminance along a first axis of the display device follows the spatial frequency;
   generating a contrast map in which contrast of each pixel is set in such a manner that the contrast gradually decreases from one end to another end along a second axis orthogonal to the first axis, and that an equal contrast line linking points having same contrast forms a given waveform; and
   generating the stimulating image by synthesizing the luminance map and the contrast map.

2. The image generation apparatus according to claim 1, wherein
   the generating the contrast map further comprises generating is the contrast map in such a manner that the equal contrast line becomes a complex wave in which a first wave and a second wave having a wavelength and amplitude larger than a wavelength and amplitude of the first wave are synthesized.

3. The image generation apparatus according to claim 2, wherein
   the generating the contrast map further comprises generating the contrast map in such a manner as to prevent a peak of the second wave from being located in a vicinity of both ends along the first axis on the contrast map.

4. The image generation apparatus according to claim 3, wherein
   the generating the contrast map further comprises obtaining contrast $C(x, y)$ of coordinates x, y from $C(x, y) = a\ y*0.5+0.5*(0.2*\sin(2\pi(x/w_1)+r_1)+\sin(2\pi(x/w_2)+r_2))$, where a represents a variable of the contrast along the second axis, $w_1$ and $w_2$ represent wavelengths of the first wave and the second wave respectively, and $r_1$ and $r_2$ represent phases of the first wave and the second wave respectively.

5. The image generation apparatus according to claim 3, wherein
   the generating the contrast map further comprises generating the contrast map so as to include a tracing accuracy measurement element that is an element in which the contrast drastically decreases from the other end to the one end along the second axis.

6. The image generation apparatus according to claim 3, the processor further configured to execute operations comprising
   determining the observation distance in such a manner that a spatial frequency in units of pixels falls under a range visually recognizable by a human when displayed on the display device, on a basis of the physical characteristic of the display device and the visual characteristic of the human.

7. The image generation apparatus according to claim 2, wherein
   the generating the contrast map further comprises obtaining contrast $C(x,y)$ of coordinates x, y from $C(x, y) = a\ y*0.5+0.5*(0.2*\sin(2\pi(x/w_1)+r_1)+\sin(2\pi(x/w_2)+r_2))$, where a represents a variable of the contrast along the second axis, $w_1$ and $w_2$ represent wavelengths of the first wave and the second wave respectively, and $r_1$ and $r_2$ represent phases of the first wave and the second wave respectively.

8. The image generation apparatus according to claim 7, wherein
   the generating the contrast map further comprises generating the contrast map so as to include a tracing accuracy measurement element that is an element in which the contrast drastically decreases from the other end to the one end along the second axis.

9. The image generation apparatus according to claim 7, further comprising
   determining the observation distance in such a manner that a spatial frequency in units of pixels falls under a range visually recognizable by a human when displayed on the display device, on a basis of the physical characteristic of the display device and the visual characteristic of the human.

10. The image generation apparatus according to claim 2, wherein
    the generating the contrast map further comprises generating the contrast map so as to include a tracing accuracy measurement element that is an element in which the contrast drastically decreases from the other end to the one end along the second axis.

11. The image generation apparatus according to claim 2, the processor further configured to execute operations comprising
    determining the observation distance in such a manner that a spatial frequency in units of pixels falls under a range visually recognizable by a human when displayed on the display device, on a basis of the physical characteristic of the display device and the visual characteristic of the human.

12. The image generation apparatus according to claim 1, wherein
    the generating the contrast map further comprises generating the contrast map so as to include a tracing accuracy measurement element that is an element in which the contrast drastically decreases from the other end to the one end along the second axis.

13. The image generation apparatus according to claim 12, further comprising
    determining the observation distance in such a manner that a spatial frequency in units of pixels falls under a range visually recognizable by a human when displayed on the display device, on a basis of the physical characteristic of the display device and the visual characteristic of the human.

14. The image generation apparatus according to claim 1, the processor further configured to execute operations comprising
    determining the observation distance in such a manner that a spatial frequency in units of pixels falls under a range visually recognizable by a human when displayed on the display device, on a basis of the physical characteristic of the display device and the visual characteristic of the human.

15. A non-transitory computer-readable recording medium on which a program is recorded for causing a computer to function as the image generation apparatus according to claim 1.

16. An image generation apparatus that generates a stimulating image to be output to a display device for measuring contrast sensitivity of a user, the apparatus comprising a processor configured to execute operations comprising:

generating a luminance map in which luminance of each pixel is set in such a manner that a change in the luminance along a first axis of the display device follows a given spatial frequency;

setting contrast of each pixel of a contrast map in such a manner that the contrast gradually decreases from one end to another end along a second axis orthogonal to the first axis, and that an equal contrast line linking points having same contrast forms a given waveform; and generating the stimulating image by coloring an image in which the luminance map, the contrast map, and a background image including at least a night sky are synthesized, so as to represent an aurora with respect to a change in the luminance.

17. A non-transitory computer-readable recording medium on which a program is recorded for causing a computer to function as the image generation apparatus according to claim 16.

18. A computer-implemented method for generating a stimulating image to be output to a display device for measuring contrast sensitivity of a user, the method comprising:

determining a spatial frequency in units of pixels within a range visually recognizable by a human when displayed on the display device, on a basis of an observation distance representing a distance between the display device and an eye of the user, a physical characteristic of the display device, and a visual characteristic of the human;

generating a luminance map in which luminance of each pixel is set in such a manner that a change in the luminance along a first axis of the display device follows the spatial frequency;

generating a contrast map in which contrast of each pixel is set in such a manner that the contrast gradually decreases from one end to another end along a second axis orthogonal to the first axis, and that an equal contrast line linking points having same contrast forms a given waveform; and generating the stimulating image by synthesizing the luminance map and the contrast map.

* * * * *

UNITED STATES PATENT AND TRADEMARK OFFICE
CERTIFICATE OF CORRECTION

| | | |
|---|---|---|
| PATENT NO. | : 12,310,658 B2 | |
| APPLICATION NO. | : 17/638812 | |
| DATED | : May 27, 2025 | |
| INVENTOR(S) | : Kenchi Hosokawa et al. | |

It is certified that error appears in the above-identified patent and that said Letters Patent is hereby corrected as shown below:

In the Claims

In Column 15, Line 32 of Claim 2, the text reading:
- generating is the contrast map -
Should read:
-- generating the contrast map --

Signed and Sealed this
Second Day of September, 2025

Coke Morgan Stewart
*Acting Director of the United States Patent and Trademark Office*